United States Patent [19] [11] Patent Number: 4,805,266
Leifeld et al. [45] Date of Patent: Feb. 21, 1989

[54] APPARATUS FOR DETECTING FOREIGN BODIES IN A MASS OF TEXTILE FIBERS

[75] Inventors: Ferdinand Leifeld, Kempen; Fritz Hösel, Mönchengladbach, both of Fed. Rep. of Germany

[73] Assignee: Trützschler GmbH & Co. KG, Mönchengladbach, Fed. Rep. of Germany

[21] Appl. No.: 150,532

[22] Filed: Jan. 29, 1988

[30] Foreign Application Priority Data

Feb. 5, 1987 [DE] Fed. Rep. of Germany ....... 3703449

[51] Int. Cl.⁴ .................. D06H 3/14; D01G 9/00; G01N 33/36; G01N 27/82
[52] U.S. Cl. .................................. 19/0.2; 19/80 R; 19/105
[58] Field of Search ............. 19/0.20, 0.23, 80 R, 19/81, 105

[56] References Cited
U.S. PATENT DOCUMENTS

| 4,167,803 | 9/1979 | Teichmann | 19/0.2 |
| 4,400,850 | 8/1983 | Burnett | 19/0.23 |
| 4,510,646 | 4/1985 | Locatelli et al. | 19/80 R |
| 4,707,887 | 11/1987 | Leifeld et al. | 19/0.2 |
| 4,731,909 | 3/1988 | Duda | 19/105 |

Primary Examiner—Louis K. Rimrodt
Attorney, Agent, or Firm—Spencer & Frank

[57] ABSTRACT

An arrangement for ascertaining the presence of foreign bodies in a mass of fiber tufts includes a fiber tuft-supporting surface having a width; a device for providing a loose fiber tuft layer on the fiber tuft-supporting surface; and a foreign body detecting apparatus arranged for scanning the fiber tuft layer for foreign bodies. The foreign body detecting apparatus has a detector device formed of a plurality of individual sensors arranged side-by-side along the width of the surface. There is further provided a device for effecting relative displacement between the fiber tuft layer and the apparatus in a direction perpendicular to the surface width.

16 Claims, 4 Drawing Sheets

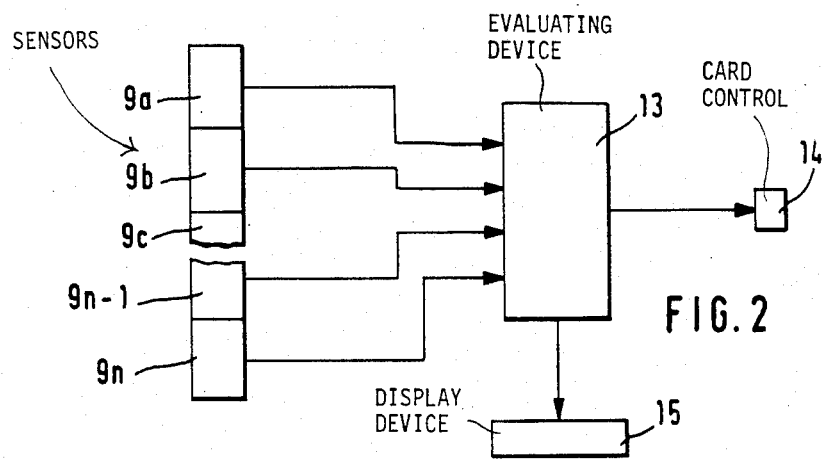
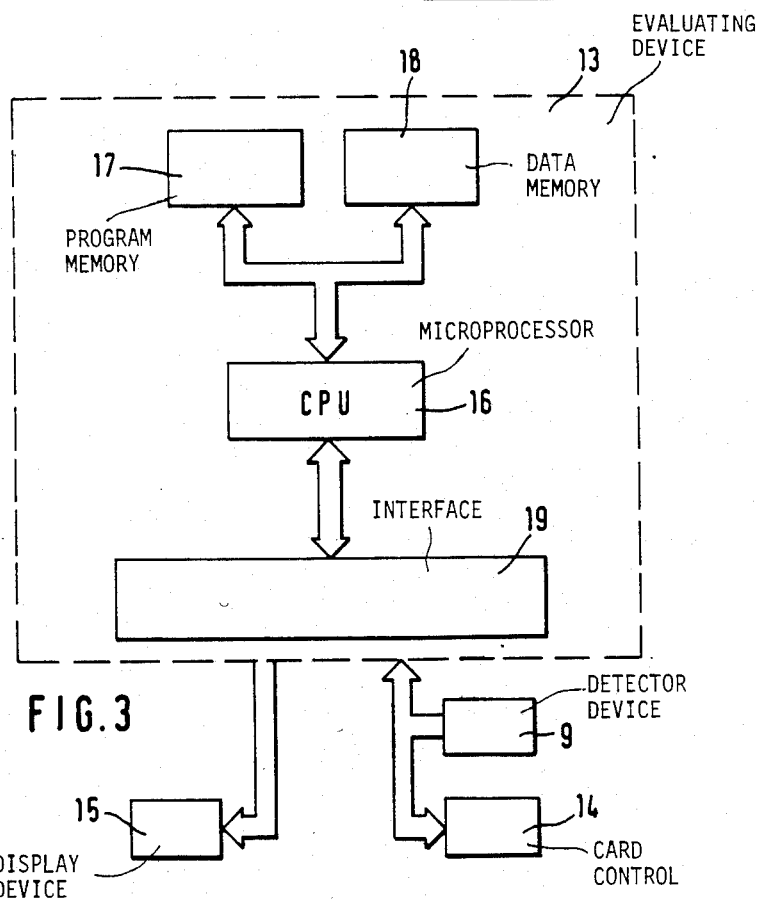

APPARATUS FOR DETECTING FOREIGN BODIES IN A MASS OF TEXTILE FIBERS

BACKGROUND OF THE INVENTION

This invention relates to an apparatus for determining the presence of foreign bodies such as metal parts, wires or the like within or between fiber tufts, particularly tufts of cotton and/or chemical fibers.

In practice, undesired foreign bodies such as metal parts, metal wires and the like can be found within or between cotton or chemical fiber tufts. Such foreign bodies adversely affect the processing of the fiber, particularly in the manufacture of high-grade yarns. During processing in cleaning and spinning installations, the foreign bodies gain access to the processing machines resulting in damages of the cylinder clothings or causing burns. The foreign bodies may be metal straps or wires with which the compressed fiber bales were tied. Frequently, the foreign bodies are found within the compressed fiber bales. Such pressed-in foreign bodies often reach through a plurality of layers (zones) so that attendants have to dig into the fiber bales manually until the entire foreign body may be lifted out. Such a procedure is very time-consuming and adversely affects a continuous processing.

In the processing of cotton, artificial fibers and other similar fiber material, it is a frequent occurrence that machine components are damaged by impurities, particularly metal objects. Such damages are particularly disadvantageous at locations where processing is performed by clothed cylinders or rollers, which may be found in cards with flats and sawtooth cleaners, etc. In machines of this type the introduction of a metal object leads to the destruction of the clothing, an interruption in the production and high repair costs.

SUMMARY OF THE INVENTION

It is an object of the invention to provide an improved apparatus of the above-outlined type which eliminates the above-discussed disadvantages and which, in particular, makes possible a reliable recognition and simple removal of foreign bodies, particularly metal parts such as wires, bands or the like.

This object and others to become apparent as the specification progresses, are accomplished by the invention, according to which, briefly stated, the fiber tufts are arranged as a loose mass and an apparatus is provided which includes a sensor assembly formed of a plurality of sensors arranged side-by-side in a series oriented parallel to the width of the fiber mass for determining the presence of foreign bodies as the fiber mass and the sensor assembly are moved relative to one another.

By providing a loose fiber tuft mass, for example, from scattering the fiber tufts from above onto a generally horizontal flat support, the foreign bodies are not bound firmly in the inside of the mass as it is the case in the pressed fiber bales but lie loosely inside or between fiber tufts so that their presence is readily recognizable. At the same time, the foreign bodies are, by virtue of the loose fiber mass, easily accessible permitting an easy removal thereof. By virtue of the fact that for determining the presence of metal foreign bodies a plurality of sensors is used along the width dimension of the fiber mass in a side-by-side relationship, an exact locating of the metallic foreign bodies is feasible since usually only one of the plurality of sensors will respond. It is a further advantage of the invention that by virtue of an exact locating of the foreign body only small quantities of fiber tufts need be removed together with the foreign body.

Additional advantageous features and alternative embodiments of the invention will be hereafter summarized.

A stationary supporting surface such as a supporting tray is provided on which the fiber tuft layer is moved relative to the stationarily held sensor assembly for detecting the presence of foreign bodies. Such a support tray is provided, for example, upstream of a material feeding device introducing the fiber mass into a cleaner or a carding machine. In the alternative, such a supporting surface may advantageously be a conveyor belt on which the scattered fiber mass is arranged and moved by the belt relative to the sensor assembly. The conveyor belt may be a sieve belt which is exposed to suction. Upstream of the supporting surface a fiber tuft feeder may be arranged which is provided with a filling chute and discharge rollers.

As sensors inductive switches, coils or the like may be used. The sensor assembly may include a single sensor roller which is in contact with the fiber tufts and which is stationarily supported. The sensor roller has an inside-disposed bank of inductive sensors. The use of such a sensor roller is advantageous in that it may compress the loose fiber tuft layer, thereby reducing the distance of the foreign metal parts within the fiber tuft layer from the upper surface thereof and thus the sensitivity of the detector system is significantly increased. The bank of inductive sensors is arranged side-by-side within the sensor roller. By virtue of the fact that the sensor roller has, along its working width, a plurality of mutually independent detectors, it is feasible to determine the location of the metal part along the width of the fiber material. By using such a sensor roller in conjunction with a fiber tuft conveying transport belt, the location of a foreign metal component may be determined with respect to the direction of conveyance and also perpendicularly thereto.

The metal detector system and the support surface or conveying device together with the fiber tuft feeder may be arranged immediately downstream of a bale opener. The metal detector device and the fiber material supporting or transporting arrangement may be situated upstream of a cleaner, a carding machine or the like.

The metal detector applies signals to an evaluating device which differentiates between foreign bodies and the fiber tufts and which processes the sensor signals to determine the location of the foreign bodies. The evaluating device applies signals to a device for removing the foreign bodies. In case the removal device provided for lifting out the foreign bodies has a plurality of individual removing elements along the width of the fiber layer supporting surface, only a very small fiber quantity needs to be removed to separate the foreign body from the fiber mass. The separating devices may be suction devices or trapdoors. The evaluating device is operatively coupled with an arrangement for shutting off the drive of the after-connected machines such as a cleaner or a carding machine.

BRIEF DESCRIPTION OF THE DRAWING

FIG 1b is a schematic side elevational view of an enlarged detail of the arrangement shown in FIG. 1a.

FIG. 2 is a block diagram illustrating the circuitry between components forming part of the invention.

FIG. 3 is a block diagram of an evaluating device forming part of the invention.

FIG. 4b is an enlarged schematic side elevational view of a detail of the arrangement shown in FIG. 4a.

DESCRIPTION OF THE PREFERRED EMBODIMENTS

Figure 1A:
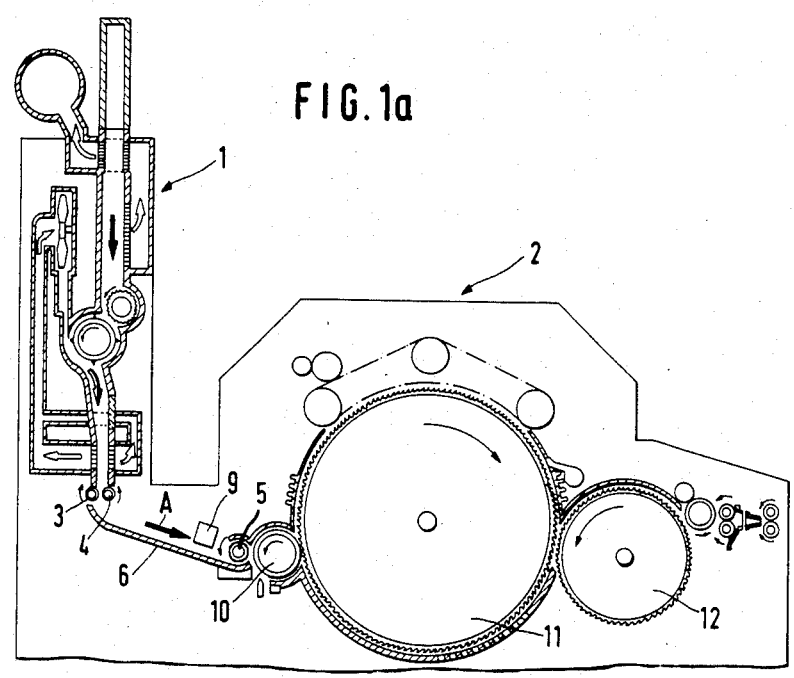
FIG. 1a is a schematic side elevational view of a tuft feeder and an after-connected carding machine, incorporating the invention.
Figure 1B:
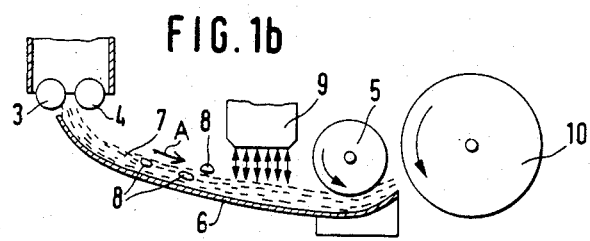
Figure 1C:
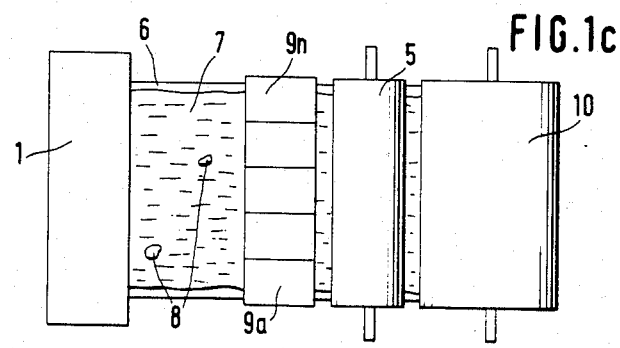
FIG. 1c is a schematic top plan view of the arrangement shown in FIG. 1b.

Turning to FIG. 1a, there is shown a tuft feeder which is generally designated at 1 and which may be an EXACTAFEED FBK model and a carding machine which is generally designated at 2 and which may be an EXACTACARD DK 715 model, both manufactured by Trützschler GmbH & Co. KG, Mönchengladbach, Federal Republic of Germany. Between the cooperating discharge rollers 3 and 4 of the tuft feeder 1 and the feed roller 5 of the carding machine 2 there extends a stationary fiber supporting transfer tray 6. As shown in more detail in FIG. 1b, a fiber tuft mass (fiber batt or fiber lap) 7 is supported on the transfer tray 6 and moves in the direction of the arrow A. Within the fiber lap 7 metallic foreign bodies 8 are shown. Above the fiber lap supporting tray 6 there is situated a detector device 9 which, as illustrated in FIG. 1c, includes a plurality of sensors 9a–9n arranged along the entire width dimension of the transfer tray 6. In operation the fiber lap 7 supported on the stationary transfer tray 6 moves relative to the stationary detector device 9. The motion of the fiber lap 7 is effected at one end by the pushing force of the discharge rollers 3 and 4 forming part of the tuft feeder 1 and is effected at the other end by the pulling force of the feed roller 5 associated with the carding machine 2. Since the detector device 9 responds to a motion of the metal bodies 8, their presence is detected in the moving fiber lap 7. The rollers of the carding machine 2, for example, the feed roller 5, the licker-in 10, the main carding cylinder 11 and the doffer 12 have a clothing (shown in FIG. 1a) which may be damaged by the foreign metal bodies 8.

Turning to FIG. 2, the sensors 9a–9n of the detector device 9 are electrically connected with an evaluating device 13 which processes the electric signals transmitted by the sensors 9a–9n for differentiating between the metallic bodies 8 and the fiber tufts of the fiber lap 7. Further, the evaluating device 13 can determine the location of the foreign body 8 with respect to the width of the transfer tray 6 by ascertaining which particular sensor 9a–9n responded to the presence of a foreign body 8. The evaluating device 13 is electrically connected with the card control 14 whereby the carding machine may be shut off by the evaluating device 13 thus preventing a foreign body 8 to be pulled into the carding machine with the fiber lap 7. The evaluating device 13 is further connected with a display device 15 which indicates the presence and/or location of the foreign body 8.

It is a particular advantage of the arrangement described above that the metal detector device 9 has a plurality of sensors 9a–9n which are arranged in a side-by-side series oriented transversely to the direction of advance of the fiber lap 7. Each of the sensors 9a–9n is connected with the evaluating device 13. If a foreign metal body 9 is situated in the fiber lap 7, one of the sensors 9a–9n responds and applies a signal to evaluating device 13 whereupon the latter stops any further material feed and indicates to the attendant the particular sector, that is, the location below the responding sensor where the foreign metal body 8 is located. The sensors 9a–9n function on the principle of inductive proximity switches and have expediently the following properties: they respond principally to moving metal components 8 and remain insensitive to the underlying stationary transfer tray 6. Further, they operate with different frequencies so that they may be situated side-by-side without interfering with one another. It is feasible to provide the sensors 9a–9n with their own internal evaluating device and a corresponding display device.

In FIG. 3 there is illustrated a block diagram for the evaluating device 13 which may be a "TMS" model microcomputer, manufactured by the firm Trützschler, comprising a central microprocessor 16, a program memory 17, a data memory 18 and an interface 19. To the evaluating device 13 there are connected the detector device 9, the display device 15 and the card control 14.

Figure 4A:
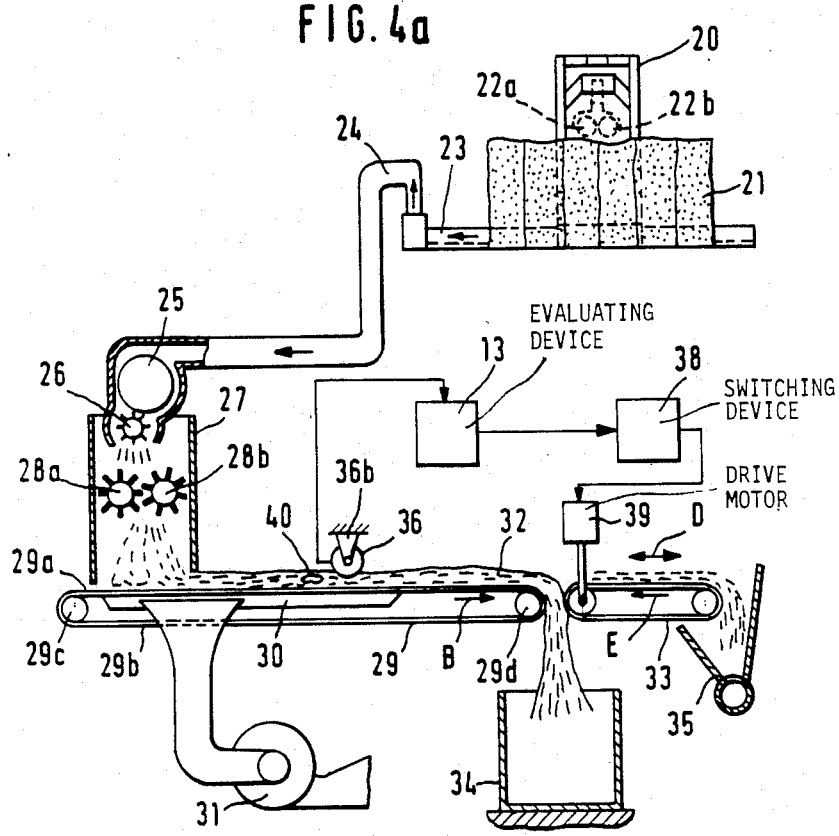
FIG. 4a is a schematic side elevational view of another preferred embodiment of the invention.
Figure 4B:
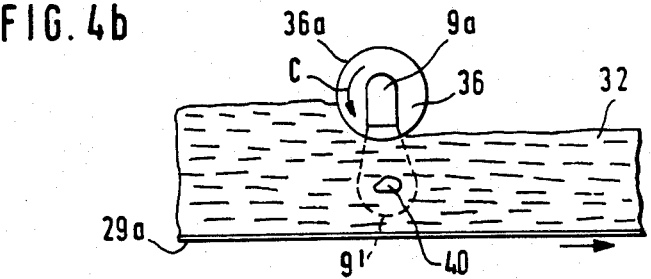

Turning to FIG. 4a, there is shown therein a bale opener 20 which may a "BLENDOMAT BDT" model manufactured by the firm Trützschler. The bale opener has an opening device which includes opening rollers 22a and 22b that travel above serially arranged fiber bales 21 and remove fiber tufts from the bale tops. The fiber tufts are pneumatically withdrawn through a channel 23 and are introduced into a conduit 24 of the condenser 25 cooperating with a stripper roller 26. The condenser 25 is arranged at the upper end of a fiber tuft fill chute 27 (fiber tuft feeder) which has two discharge rollers 28a and 28b. Underneath the tuft fill chute 27 a conveyor belt 29 formed of a sieve belt is arranged. Between the upper and lower flights 29a and 29b of the conveyor belt 29 a suction hood 30 is provided which exposes the upper reach 29a, moving in the direction of arrow B, to vacuum and which is connected with the suction side of a fan 31. The loose fiber tuft layer 32 on the upper reach 29a of the conveyor belt 29 is relatively thin. Downstream of the conveyor belt 29 a further conveyor belt 33 is arranged. Between the two conveyor belts 29 and 33 an intermediate space is present under which a waste container 34 is situated. At the downstream end of the second conveyor belt 33 there is provided a suction device 35 for removing the fiber tufts. Above the upper reach 29a of the conveyor belt 29 a sensor roller 36 is arranged which functions as a metal detector and which presses down on the loose fiber layer 32. The sensor roller 36a is rotatably held in a stationary bearing 36b. As shown in FIG. 4b, the sensor roller 36 is a hollow cylinder having a cylindrical wall 36a which rotates as indicated by the arrow C. The cylindrical wall 36a is, similarly to the conveyor belt 29, made of a non-metallic material. In the inside of the sensor roller 36 there is arranged a plurality of sensors 9a-9n in a side-by-side relationship. The effective zone of the sensors 9a-9n is designated at 9', while the foreign body is designated at 40. The sensor roller 36 applies its signals to the evaluating device 13 which differentiates the foreign bodies from the fiber tufts and a switching device 38 which is connected with the drive motor 39 of the conveyor belt 33. The drive motor 39 may effect a reversal of the motion of the transport belt 33, so that the latter may be selectively moved in either direction indicated by the double-headed arrow D. When, upon a signal from the switching device 38—which responded because a foreign body was detected—the motor 39 is reversed, the upper reach of the conveyor belt 33 moves in the direction of the arrow E whereby one part of the fiber material situated on the upper reach 29a of the conveyor belt 29 and containing a foreign body 40 falls into the waste container 34 rather than being admitted to the conveyor belt 33 and the suction device 35.

In operation the fill chute 27 delivers fiber tufts in a downward direction over a width of approximately 1 meter. Underneath the discharge opening of the fill chute 27 there is situated the upper reach 29a of the conveyor belt 29, exposed to suction. The sieve belt is driven by end rollers 29c, 29d in the direction of the arrow B. The belt drive motor, whose speed is variable, may be connected with the end roller 29c while the end roller 29d may be idling. By virtue of this arrangement a relatively uniform scattered fiber tuft layer 32 may be obtained whose density may be adapted in a desired manner by varying the conveying speed of the sieve belt. By virtue of the suction generated by the suction device 30 the fiber tuft layer 32 is compressed and thus its upper surface is reduced and further, during movement of the conveyor belt 29 there is no significant relative displacement between the belt 29 and the fiber layer 32. The sensor roller which includes the sensors 9a-9n contacts the fiber material 32 along its entire length and seeks out the foreign bodies 40. In the evaluating device 13 the foreign bodies are recognized as such and their location is pinpointed.

Figure 5:
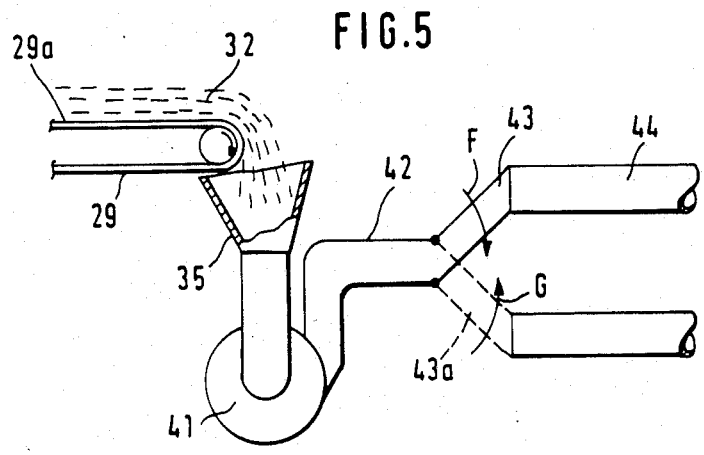
FIG. 5 is a schematic side elevational view of a preferred embodiment for removing foreign bodies from a fiber tuft mass.

Turning to FIG. 5, a suction device 35 is connected with the conveyor belt 29 and is also coupled by means of a fiber material conveyor fan 41 with a duct 42. The duct 42 is adjoined by a routing gate 43 which is operatively connected with a switching device comparable to the switching device 38 operating the motor 39 of the embodiment shown in FIG. 4a. When a foreign body 40 is detected in the fiber material 32, the switching device applies a signal to a drive (not shown) for the routing gate 43 which is thereupon pivoted into the dash-dotted position 43a.

Figure 6:
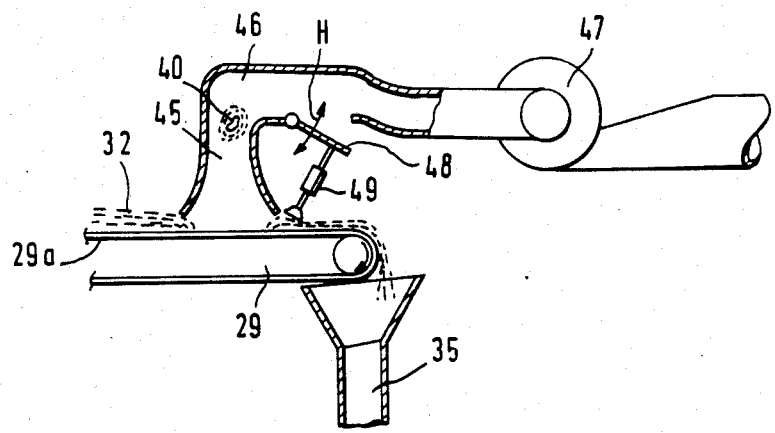
FIG. 6 is a schematic side elevational view of another preferred embodiment for removing foreign bodies from a fiber tuft mass.

Turning to FIG. 6, there is illustrated a further embodiment by means of which, after recognizing a foreign body 40, a suction nozzle 45 removes as waste the fiber tufts containing the foreign body 40, from the belt 29 at a location downstream of the detector device (not shown in FIG. 6). The suction nozzle 45 is in communication by means of a conveyor duct 46 with the intake side of a fan 47. In the duct 46 there is arranged a pivotal gate 48 whose driving device 49 is connected with the switching device corresponding to the switching device 38. When a foreign body 40 is detected in the fiber material 32, the switching device emits a pulse and applies it to the driving device 49 for the gate 48 which thereupon is pivoted downwardly in the direction of the arrow H so that the fiber material, together with foreign body, is separated from the conduit 46. In case the suction nozzle 45 has a plurality of individual sections along the width and the foreign body detector device has a plurality of sensors also arranged along the width of the travelling fiber material, only very small fiber tuft quantities of the layer 32 are separated together with the foreign body 40. For the removal there is only that sector of the suction device 45 connected operatively to the fan 47 which is situated above the zone of the fiber tuft layer 32 in which the metal component has been detected.

It will be understood that the above description of the present invention is susceptible to various modifications, changes and adaptations, and the same are intended to be comprehended within the meaning and range of equivalents of the appended claims.

What is claimed is:

1. An arrangement for ascertaining the presence of foreign bodies in a mass of fiber tufts, comprising
    (a) a fiber tuft-supporting surface having a width;
    (b) means for providing a loose fiber tuft layer on said surface;
    (c) a foreign body detecting apparatus arranged for scanning the fiber tuft layer for foreign bodies; said foreign body detecting apparatus comprising a detector device formed of a plurality of individual sensors arranged side-by-side along said width; and
    (d) moving means for effecting relative displacement between said fiber tuft layer and said apparatus in a direction perpendicular to said width.

2. An arrangement as defined in claim 1, wherein each individual sensor has a sensing range extending into the fiber tuft layer; the sensing ranges of respective said sensors being situated substantially side-by-side along said width.

3. An arrangement as defined in claim 1, further comprising a stationarily held transfer tray having an upper face constituting said fiber tuft supporting surface.

4. An arrangement as defined in claim 1, further comprising a belt conveyor including a generally horizontally-oriented conveyor belt having an upper conveying face constituting said fiber tuft supporting surface; said detector device being vertically spaced from said upper conveying face and being stationarily supported, whereby said fiber mass transported by said conveyor belt moves relatively to said detector device.

5. An arrangement as defined in claim 4, wherein said conveyor belt is a sieve belt; further comprising suction means situated underneath said upper conveying face for pressing the fiber tuft layer against said upper conveying face.

6. An arrangement as defined in claim 1, wherein said means for providing a loose fiber tuft layer comprises a vertical fiber tuft feeder arranged above said fiber tuft-supporting surface.

7. An arrangement as defined in claim 1, wherein said sensors are inductive switches.

8. An arrangement as defined in claim 1, wherein said switches comprise inductive coils.

9. An arrangement as defined in claim 1, wherein said detector device comprises a scanner roller extending along said width and being arranged for contacting said fiber tuft layer.

10. An arrangement as defined in claim 9, wherein said individual sensors are situated within said scanner roller.

11. An arrangement as defined in claim 1, in combination with a fiber bale opener, wherein said foreign body detecting apparatus and said fiber tuft-supporting surface are arranged immediately downstream of said bale opener as viewed in the direction of a fiber tuft flow from the bale opener.

12. An arrangement as defined in claim 1, in combination with a carding machine, wherein said foreign body detecting apparatus and said fiber tuft-supporting surface are arranged immediately upstream of said carding machine as viewed in a direction of a fiber tuft flow into said carding machine.

13. An arrangement as defined in claim 1, in combination with a cleaner, wherein said foreign body detecting apparatus and said fiber tuft-supporting surface are arranged immediately upstream of said cleaner as viewed in a direction of a fiber tuft flow into said cleaner.

14. An arrangement as defined in claim 1, wherein said foreign body detecting apparatus includes an evaluating device connected to said sensors for receiving signals therefrom for determining the location of a detected foreign body along said width.

15. An arrangement as defined in claim 14, further comprising a foreign body removing apparatus operatively connected to said evaluating device for being actuated upon detection of a foreign body by said detector device.

16. An arrangement as defined in claim 14, in combination with a fiber processing machine receiving fiber tufts from said layer; said fiber processing machine having a drive; further comprising a switching device connected to said evaluating device and said drive for shutting off said drive upon detection of a foreign body by said detector device.

* * * * *